(12) United States Patent
Toda

(10) Patent No.: US 6,937,736 B2
(45) Date of Patent: Aug. 30, 2005

(54) ACOUSTIC SENSOR USING CURVED PIEZOELECTRIC FILM

(75) Inventor: Minoru Toda, Lawrenceville, NJ (US)

(73) Assignee: Measurement Specialties, Inc., Fairfield, NJ (US)

( * ) Notice: Subject to any disclaimer, the term of this patent is extended or adjusted under 35 U.S.C. 154(b) by 276 days.

(21) Appl. No.: 10/212,557

(22) Filed: Aug. 5, 2002

(65) Prior Publication Data
US 2003/0028110 A1 Feb. 6, 2003

Related U.S. Application Data

(60) Provisional application No. 60/310,284, filed on Aug. 6, 2001.

(51) Int. Cl.[7] .............................................. H04R 25/00
(52) U.S. Cl. ....................................... 381/190; 310/367
(58) Field of Search .............................. 310/324, 327, 310/330, 338, 348, 367, 371

(56) References Cited

U.S. PATENT DOCUMENTS

| 2,121,779 | A | 6/1938 | Ballantine |
| 4,186,323 | A | 1/1980 | Cragg et al. |
| 4,379,211 | A | 4/1983 | Joscelyn et al. |
| 4,429,191 | A | 1/1984 | Busch-Vishniac et al. |
| 4,440,983 | A | 4/1984 | Facoetti et al. |
| 4,453,044 | A | 6/1984 | Murphy |
| 4,535,205 | A | 8/1985 | Ravinet et al. |
| 5,195,142 | A | 3/1993 | D'Avolio et al. |
| 5,283,835 | A | 2/1994 | Athanas |
| 6,111,967 | A | 8/2000 | Face, Jr. et al. |
| 6,159,166 | A | 12/2000 | Chesney et al. |
| 6,201,874 | B1 | 3/2001 | Croft, III et al. |

Primary Examiner—Curtis Kuntz
Assistant Examiner—Brian Ensey
(74) Attorney, Agent, or Firm—Plevy, Howard & Darcy PC

(57) ABSTRACT

An acoustic sensor device comprising a substrate having a first surface and a second surface opposite the first surface, and an aperture formed therethrough, the second surface having a curved portion; a layer of piezoelectric film having a first surface disposed on the curved portion of the substrate second surface; and a layer of pliable material disposed on a second surface of the piezoelectric film opposite the first surface for contacting with an object to be sensed.

20 Claims, 9 Drawing Sheets

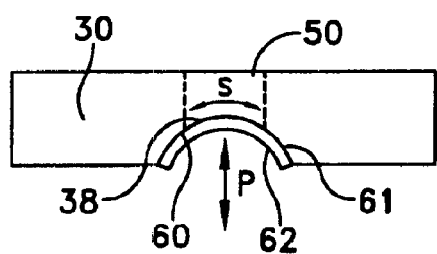
FIG. 1A
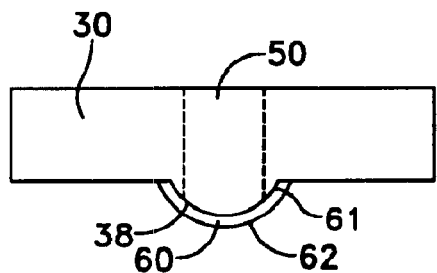
FIG. 1B
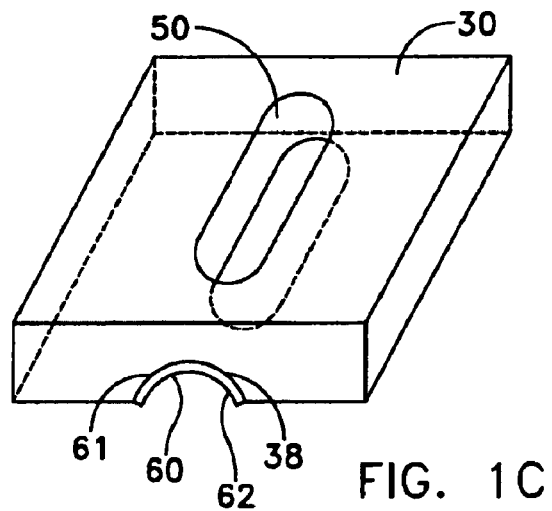
FIG. 1C
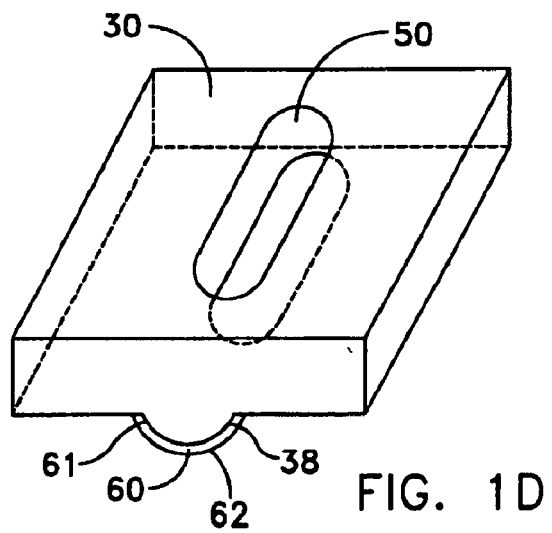
FIG. 1D
FIG. 1

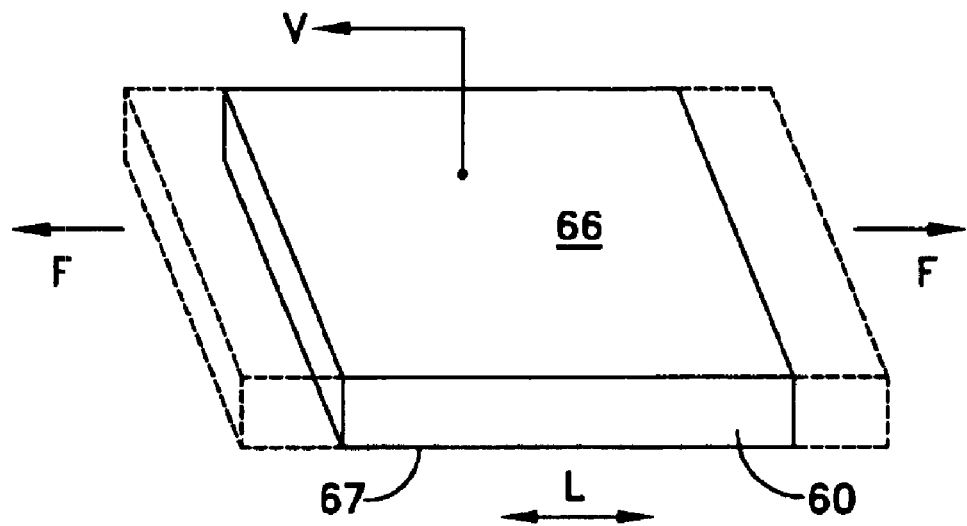
FIG. 3A
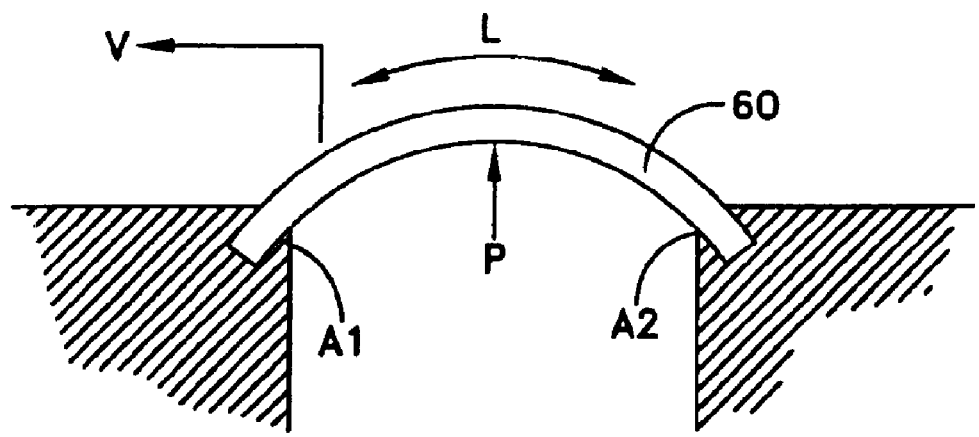
FIG. 3B
FIG. 3

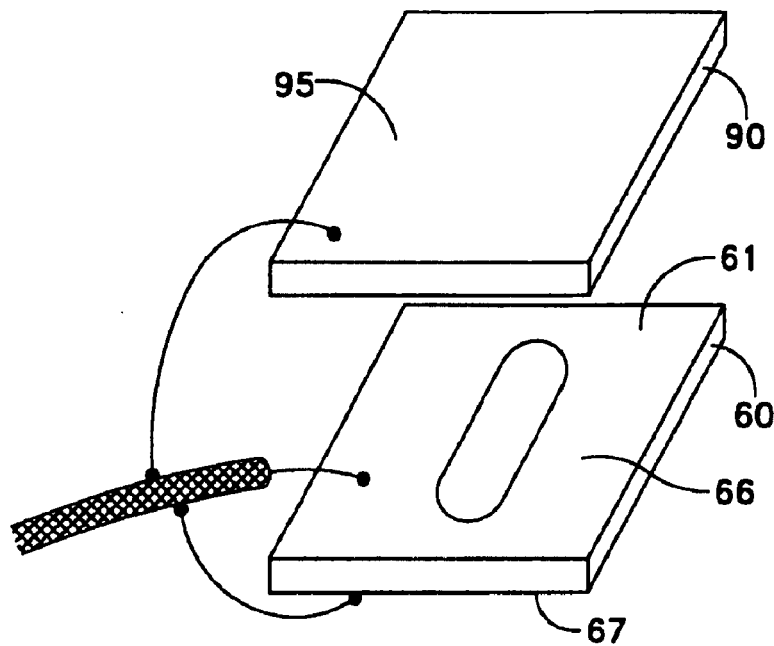
FIG. 8A
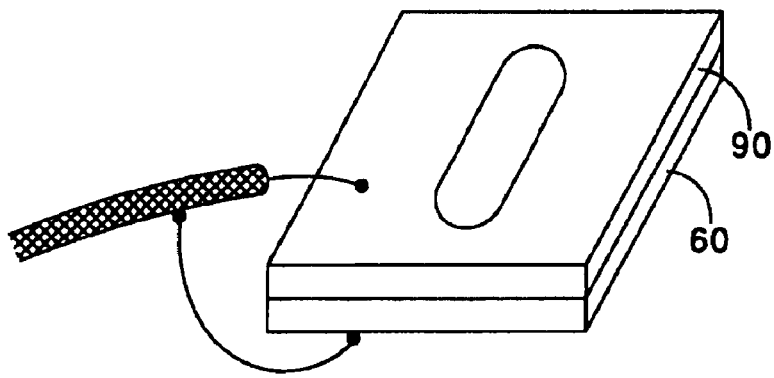
FIG. 8B
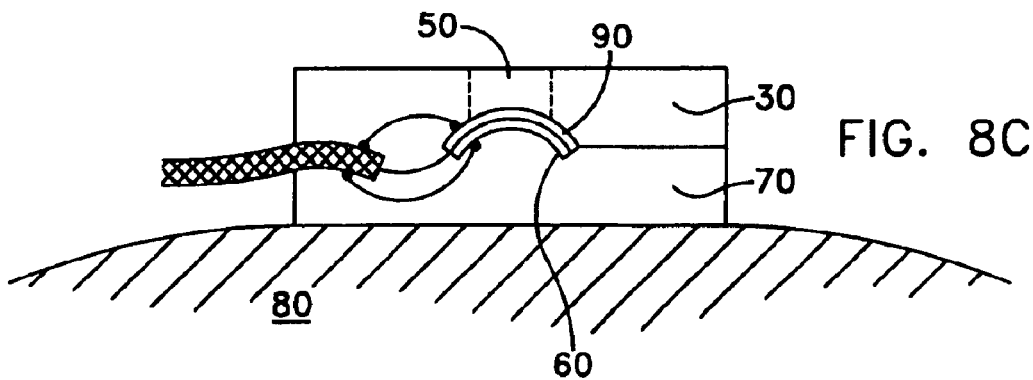
FIG. 8C
FIG. 8

ACOUSTIC SENSOR USING CURVED PIEZOELECTRIC FILM

PRIORITY FILING

This application claims priority from co-pending Provisional Patent Application Ser. No. 60/310,284 entitled "Contact Microphone Using Curved Piezo Film", filed on Aug. 6, 2001.

FIELD OF THE INVENTION

The present invention relates generally to sensor devices and more particularly, to a vibration sensor for detecting acoustic information.

BACKGROUND OF THE INVENTION

An electronic stethoscope or contact microphone operates as a vibration sensing element contacted to a body part such as a person's skull or attached to one's neck or throat, for example, so as to detect sound propagating through tissue, muscle, tendon, ligament, and bone. In this way, an acoustic signal (e.g. a voice signal) is detected by the sensor. In conventional microphone systems, noise is frequently a problem. It is particularly troublesome in high noise environments, for example, in factories, construction sites, engine rooms, and the like.

In medical diagnostic systems employing acoustic sensors, a typical acoustic device is a stethoscope which operates to detect sound generated in internal organs. Its ability to direct sound transmission to a sensing element without interference from external noise is very important. Other medical applications include continuous monitoring of a patient's acoustic signals, for example, in order to quickly detect and alert medical personnel to any abnormal signals indicative of a patient's health.

Conventional contact microphones utilize a structure comprising a rubber cylinder of diameter D, having a flat, top end surface and a bottom end surface opposite one another. A layer of polyvinylidene fluoride (PVDF) film is wrapped around the curved side of the cylinder. The first end surface of the rubber is contacted to the skin while the other is connected to a holder. When vibrations are transmitted to the contacted end, the diameter of the rubber cylinder expands or shrinks depending on the vibration. The PVDF material surrounding the cylinder detects the diameter variation. However, the process of wrapping PVDF onto a cylinder and bonding to it to form such an acoustic device is a difficult task in terms of mass producing these devices within predetermined working requirements and tolerances. Consequently, the cost of producing such devices becomes expensive. A need exists to obtain a low cost and efficient method of forming a device having a sensitivity similar to that of conventional contact microphones formed of cylindrical rubber surrounded or wrapped by a layer of PVDF.

Conventional contact microphones are also formed having a thick layer of PVDF-TrFE copolymer used as the piezoelectric element. A backside of the layer is bonded to a plate which acts as a mass. The front side of the copolymer layer is directly contacted to the skin of a person. Vibrations transferred through the skin induce pressure variations to the sensor such that the thickness of the copolymer layer is expanded or contracted, thereby generating a voltage signal. In order to obtain the necessary sensitivity for medical applications, the thickness of the copolymer layer has be on the order of a few millimeters. A significant drawback associated with this type of device is that the cost to produce the thick copolymer layer is much higher than that of PVDF film.

An apparatus having a sensitivity which is similar to or greater than that of the thick copolymer layer and having a production cost substantially lower than conventional devices is highly desired. It is also desired to obtain an apparatus that is less susceptible to acoustic interference than conventional contact microphones.

SUMMARY OF THE INVENTION

An acoustic sensor device has a substrate having a first surface and a second surface opposite the first surface, and an aperture formed therethrough, the second surface also having a curved portion. A layer of piezoelectric film having a first surface is disposed on that curved portion of the substrate second surface. A second surface of the piezoelectric film, which is opposite the first surface, has a layer of pliable material disposed on it, for contacting with an object to be sensed.

According to another aspect of the invention, the acoustic sensor device further has a housing for holding the substrate, piezoelectric film and pliable material. The housing has an opening through which a portion of the pliable material protrudes for contacting with an object to be sensed.

In yet another aspect of the invention, a polymer layer is disposed on a surface of the piezoelectric film, for shielding of the piezoelectric film from electrical noise.

It is embodied in still another mode of the invention a method of sensing an acoustic signal including the steps of forming an acoustic sensor device having a substrate with a first surface and a second surface opposite the first surface and an aperture formed therethrough, and also having a layer of piezoelectric film with a first surface and a second surface opposite the first surface, the first surface being disposed on a curved portion of the substrate second surface and the second surface being disposed on a layer of pliable material; contacting the layer of pliable material with an object to be sensed; causing, through transmission of the sensed acoustic signal, an application of pressure on the piezoelectric film in a direction substantially normal to a surface of the film; and generating, through the piezoelectric effect of the film, an electrical signal indicative of the acoustic signal.

BRIEF DESCRIPTION OF THE FIGURES

FIGS. 1A–1D show side and perspective views of each of the substrate and piezoelectric layer elements embodied in the present of the invention;

FIGS. 3A–3B illustrate the basic principle of operation of the device;

FIGS. 8A–8C show a shielded sensing device structure according to an alternate embodiment of the present invention.

DETAILED DESCRIPTION OF THE INVENTION

Figure 2:
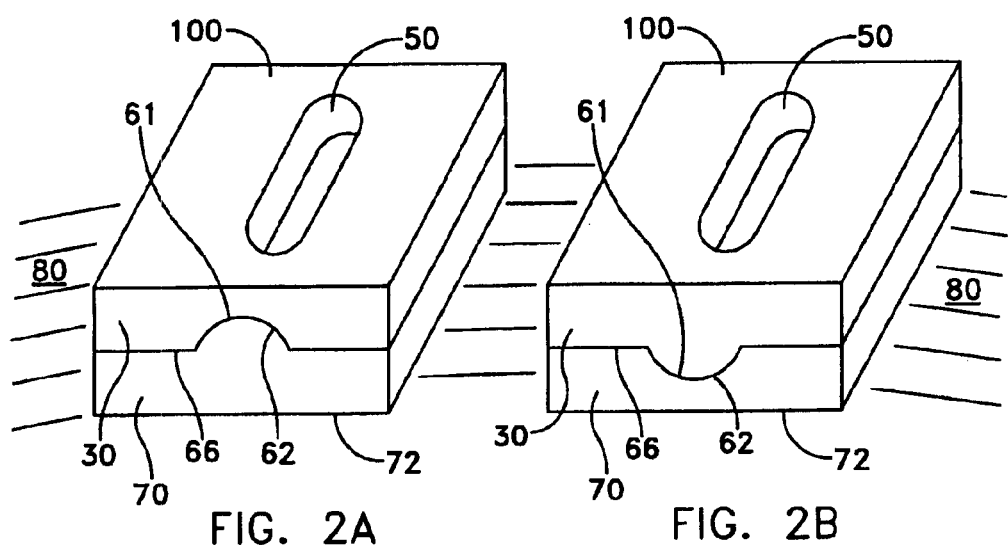
FIGS. 2A–2B show exemplary embodiments of a formed sensing device having concave and convex curved surfaces respectively.

Referring generally to FIGS. 1 and 2, a device 100 according to an aspect of the present invention is formed and operated as follows. A plate or substrate 30 is formed of a stiff material such as metal or plastic, and has an aperture 50 formed therein. The aperture or hole may take on a variety of shapes, and may be round or oval, for example. The aperture is formed substantially at the center of the plate.

At least a portion 38 of one side of the plate is curved to a concave or convex shape. A layer 60 of piezoelectric polymer material, such as PVDF film, has a first surface 61 and a second surface 62 opposite the first surface. The first surface 61 of the film is disposed over portion 38 and the hole 50 of the substrate 30, such that the molecular chain direction of the PVDF film is along the curved direction. An adhesive located at the periphery of the hole may be used to attach the PVDF film to the substrate. Other attaching means as known in the art may also be used.

A pliable layer 70 such as a soft rubber type material is disposed on side 62 of the PVDF film. Outer surface 72 of layer 70 is contacted to the skin surface 80, causing a vibration to be transmitted to the PVDF surface. The vibration generates acoustic pressure P at the surface of the piezoelectric film which yields a displacement normal to the film surface. Since the periphery of the PVDF is bonded to the stiff holder or substrate, the length of the PVDF in the molecular chain direction (i.e. the curved direction) has to expand or shrink. This strain S generates a voltage signal. Electrode layers coupled to the PVDF operate to carry the voltage signal indicative of acoustic transmission to remote electronic circuitry for processing.

This piezoelectric effect principle is illustrated in FIG. 3A. When a force F is applied to the PVDF material 60 along its length direction L, which is the molecular chain direction, a strain results and an electric field is generated in the thickness direction. A resulting voltage signal V is detected on the electrodes 66 and 67 on both surfaces.

In the aspect of the invention depicted in FIGS. 2A–2B, the active electrode 66 may have a shape which matches the shape of the plate aperture 50. The length direction is defined by the machined direction (during film formation, it is stretched and molecules align to that stretching direction). When the PVDF film is curved along the length direction L with its two ends at points A1 and A2 fixed, as shown in FIG. 3B, the pressure P normal to the surface is converted to stress or strain along its length and a voltage signal V is generated on the surface electrode. The curving of the PVDF film along the length direction results in a greater stress response, as compared to film stressed in a flat configuration, as shown in FIG. 3A, having an applied force parallel to the plane.

Figure 4:
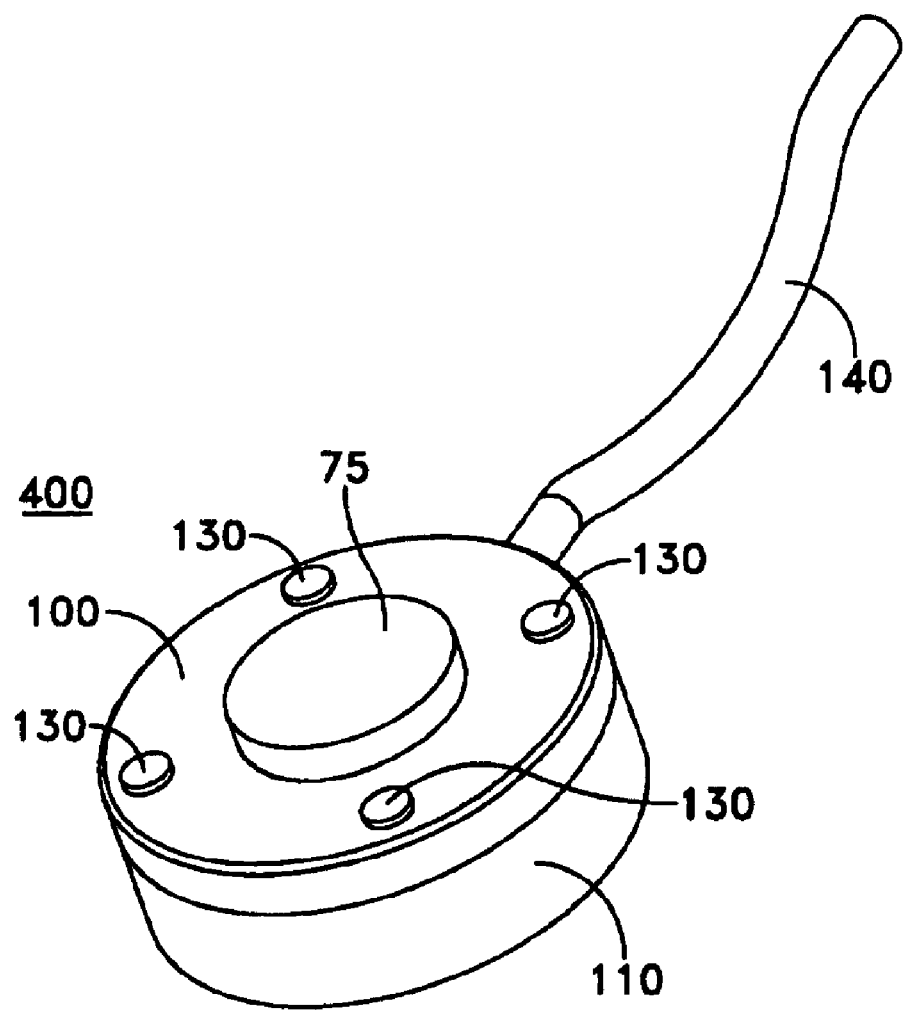
FIG. 4 is a perspective view of an acoustic sensor device embodying the principles of the present invention.

FIG. 4 shows one mode of the present invention, embodying the above-mentioned principle. The acoustic sensor device 400 comprises a housing top portion 100 and bottom portion 110, fasteners 130 for the housing, a protruding portion 75 of a pliable layer and a shielded cable 140 containing lead wires.

Figure 5:
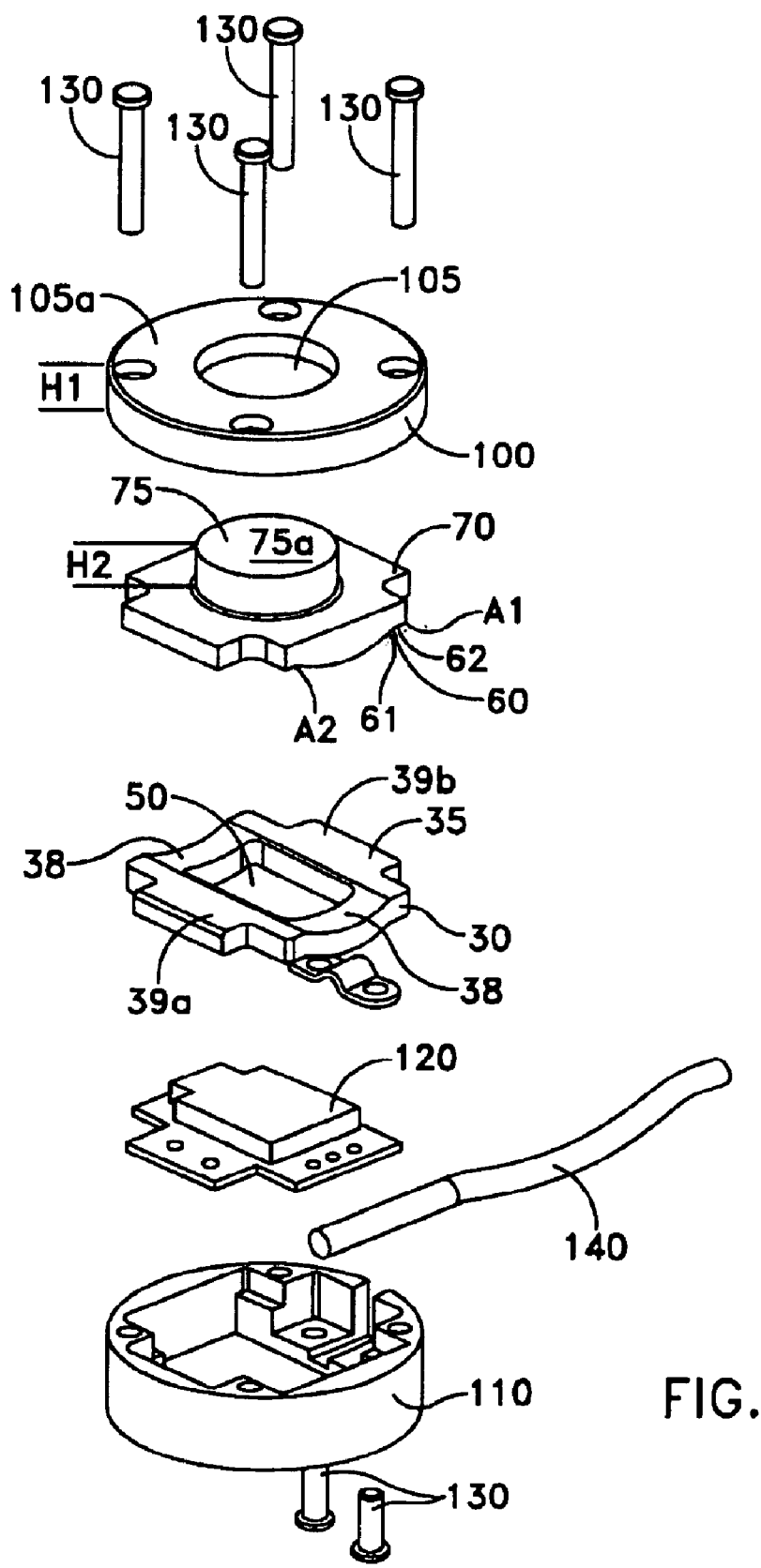
FIG. 5 is a perspective, exploded view of the acoustic sensor device illustrated in FIG. 4.

FIG. 5 provides a corresponding exploded view of the device shown in FIG. 4. As shown in detail in FIG. 5, a stiff plate 30 formed of a metal (e.g. stainless steel, iron, brass, aluminum) or plastic (e.g. poly carbonate, acrylic, ABS) for example, has a center hole 50 formed therein. One side surface 35 of the plate has concave curved regions 38. As described above for FIGS. 1 and 2, the device according to the present invention may also be formed as a convex structure. A layer of piezoelectric film 60 such as PVDF film of, for example 28 to 110 microns (um) thickness has first surface 61 disposed on a portion of the side surface 35 of the plate, including especially the curved region 38. The first surface 61 of the film is disposed in such a manner that the film spans the aperture or center hole 50.

On the second surface 62 of PVDF film 60, a pliable layer 70 of material covers the film without any gap or void. The pliable layer may comprise silicone rubber or other soft rubber type material, such as polyurethane or soft polyethylene. As described above for FIGS. 1 and 2, the pliable layer 70 has a curved portions such that when the film is disposed on it, the first surface 61 of the film conforms with the curved portions 38 of the plate 30. This arrangement results in the curving of the PVDF film along the length direction with its two ends at points A1 and A2 fixed, as described above for FIG. 3B.

The pliable layer 70 shown in FIG. 5 may be made by chemical reaction of a liquid form of rubber to convert it to a pliable rubber form. This is accomplished by pouring a liquid with a suitable reaction agent already mixed onto the stiff plate 30 having the PVDF film disposed thereon. The four sides of the stiff plate 30 are surrounded by a wall (not shown) to prevent the liquid from spilling over. After a wait time, the liquid cures and the rubber is formed. The wait time depends on the material, and the cure may take place by moisture absorption from the air or evaporation of a volatile component.

The device depicted in FIG. 5 also comprises a housing having a top portion 100 and a bottom portion 110. The top portion 100 has an opening 105, through which a protruding portion 75 of the rubber layer 70 projects outwardly, for contacting with the object to be sensed, such as the skin surface. The device also has a printed circuit board 120, positioned between the substrate 30 and the bottom portion 110 of the housing, which may have an optional buffer circuit for signal conditioning. A shielded cable 140 contains lead wires from the printed circuit board 120, which connects to remote electronic circuitry.

The housing, assembled with standard fasteners 130 known in the art, may also apply some pressure to the contained components and serve to pressure clamp the first surface 61 of the PVDF film to the non-apertured regions of the plate 30 or support member. In this mode, clamping, rather than an adhesive, is used to attach the PVDF film to the periphery of the plate surface 35. In particular, the assembly of the housing results in pressure being applied to the portions of PVDF film corresponding with the non-apertured regions of the plate 30. This applied pressure results in the fixing of the PVDF film 60 to the plate 30 at those regions, while leaving the regions spanning the aperture 50 movable, in order to receive the acoustic vibrations.

Other attaching means as known in the art may also be used. Although the PVDF film may remain somewhat movable with respect to the curved portions 38 of the plate 30, it is necessary for the film to be fixed to the plate at the non-curved sides 39a and 39b, in order to maintain the curvature of the PVDF in the length direction. This design causes the expansion or shrinkage of the film to occur in the length, or molecular chain direction, thereby maximizing the direct piezoelectric effect. This principle of fixing the PVDF film at two points is also illustrated in FIG. 3B.

The surface of the rubber layer 75a, as it protrudes through the housing top portion 100, is contacted to a person's skin and an acoustic wave is produced from an internal organ. The surface 75a may be parallel with a surface 105a of the housing top portion, for this purpose. In the subject embodiment, the height H1 of the protruding portion 75 is slightly greater than the height H2 of the housing top portion 100, such that the protruding portion 75 projects through the hole 105 in the housing. In an alternate embodiment, the heights H1 and H2 may be the same, such that surface 75a is coplanar with surface 105a, allowing both surfaces to substantially evenly contact the skin surface to receive the acoustic signal.

Since the acoustic impedance of the rubbery material is relatively close to that of human tissue (i.e. on the order of $1.5 \times 10^6$ kg/m$^2$·sec), acoustic waves propagate through the boundary between the skin and the pliable layer 70, with minimal reflection loss. The boundary between the skin and pliable portion 75 may additionally be filled with an enhancing medium such as a grease or an acoustic gel, but such a medium is not required in the present invention. Other materials having similar acoustic impedances may also be used in place of the rubber layer, such as polyurethane, for example.

As described above, the acoustic vibrations generate acoustic pressure at the piezoelectric film second surface 62, yielding a displacement which is normal to the film surface. The resultant strain in the piezoelectric film 60 occurs in the length, or curved, direction and generates a voltage signal. The pressure sensitivity (voltage output per unit pressure of the device) is given by $V=Rd31/\epsilon\epsilon0$, where R is the curvature radius, d31 is the piezoelectric strain constant, $\epsilon$ is the relative dielectric constant of PVDF and $\epsilon0$ is that of a vacuum.

Typically, the sensitivity of a PVDF device increases for thicker layers of PVDF, because the same electric field leads to greater voltages for thicker films. However, in the present device, the strain due to applied pressures decreases for thicker films because thicker films are stiffer and deform less easily. In thicker films, this reduction in strain cancels out the higher voltage effects. Therefore the sensitivity equation does not have a thickness term.

The sensitivity of the subject invention is an improvement over that of conventional contact microphones, which utilize a structure comprising a rubber cylinder with a layer of PVDF film wrapped around the cylinder side. In the case of such conventional microphones, when the rubber end contacts the human body, the piezoelectric film experiences an indirect force applied radially from that rubber end. However, in the subject invention, the piezoelectric film experiences an actual force applied in a direction normal to its surface. This application of direct force results in a higher sensitivity.

Additionally, manufacturing cost demands are lower, since the present invention utilizes a simple configuration. There is no need to join the two ends of the PVDF film when wrapping it around a rubber cylinder, or to compress the cylinder to provide such an arrangement, as in the prior art. Also, as noted above, the invention does not require thicker, more expensive layers of piezoelectric material in order to achieve higher sensitivities. Nor does it need to utilize expensive, thick layers of copolymers as required by other conventionally known devices.

Figure 6:
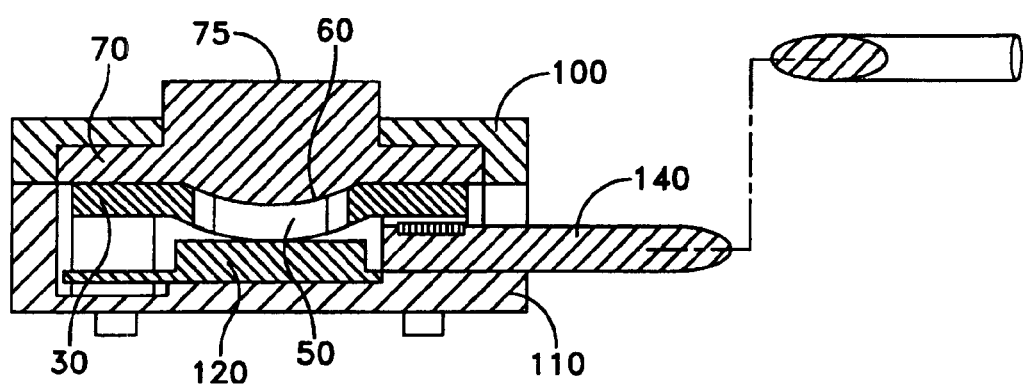
FIG. 6 is an assembled sectional view of the device shown in FIG. 4.
Figure 7:
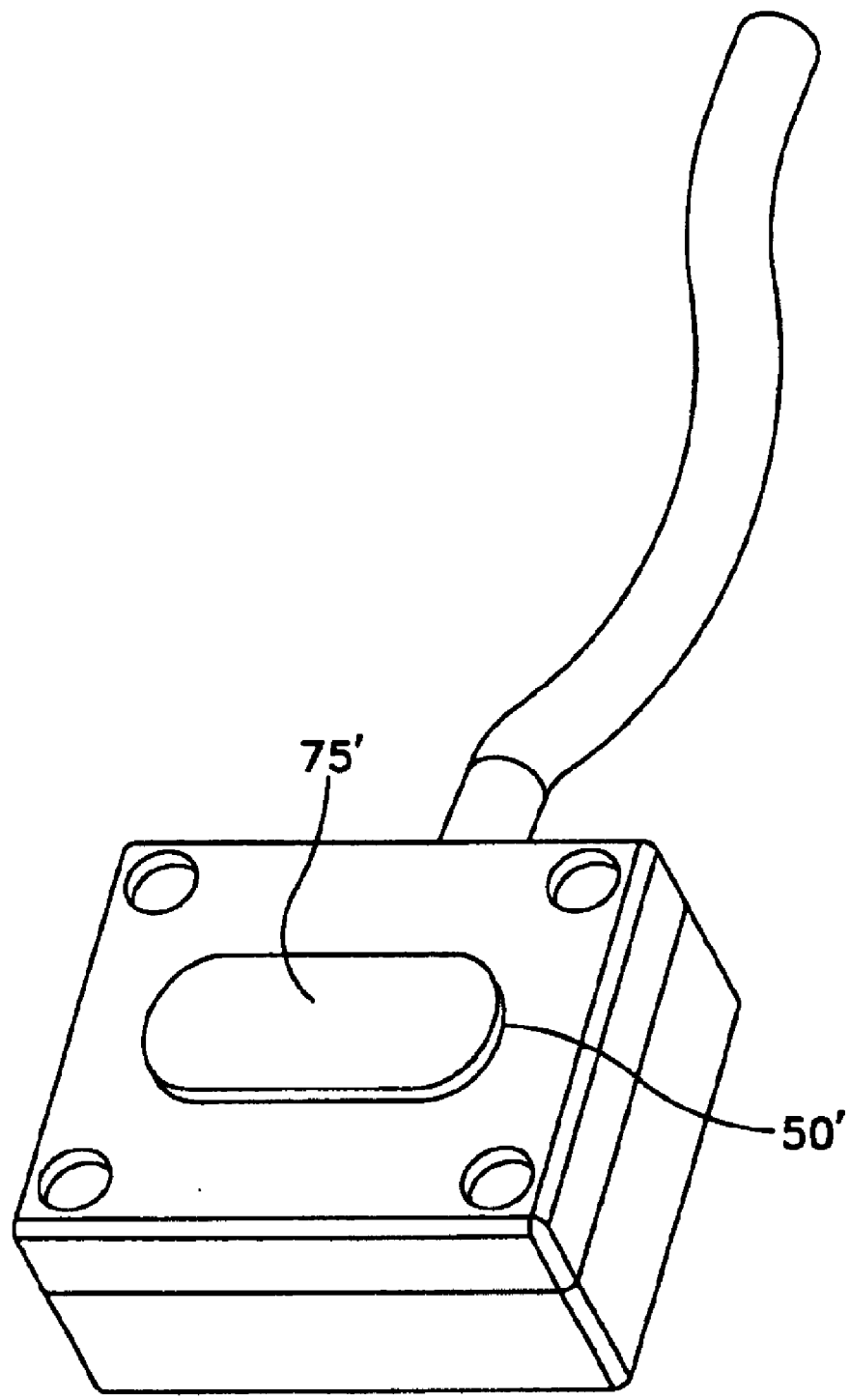
FIG. 7 is a perspective view of an alternative embodiment illustrating an acoustic sensor device having a rectangular structure.

FIG. 6 depicts an assembled, sectional view of the mode illustrated in FIGS. 5 and 6, showing the various component layers held within the housing, including the PVDF layer 60. The mode of the invention shown in FIG. 7 incorporates a similar design to that in FIGS. 4–6, but utilizing a rectangular structure and having an oval shaped opening 50' for protruding portion 75' of the pliable layer.

In an alternate embodiment shown in FIGS. 8A–8C, the device of the present invention may have its sensing element shielded to reduce noise, such as external electrical noise that may be encountered during the operation of the device. For this purpose, another polymer film 90 is bonded to the first surface 61 of the PVDF film 60. The bonding may be accomplished by use of an epoxy. The additional film should be sufficiently soft or pliable so as not to significantly reduce the strain induced by the acoustic pressure. A typical soft material used for such purposes is polyethylene, at a typical thickness of approximately 100 microns. The first surface electrode 66 of the PVDF film is configured as an active electrode, while both the top surface electrode 95 of the polymer film and the second surface electrode 67 are connected to ground. This configuration effectively serves to shield the PVDF film from exposure to external electrical noise through the aperture 50.

Figure 9:
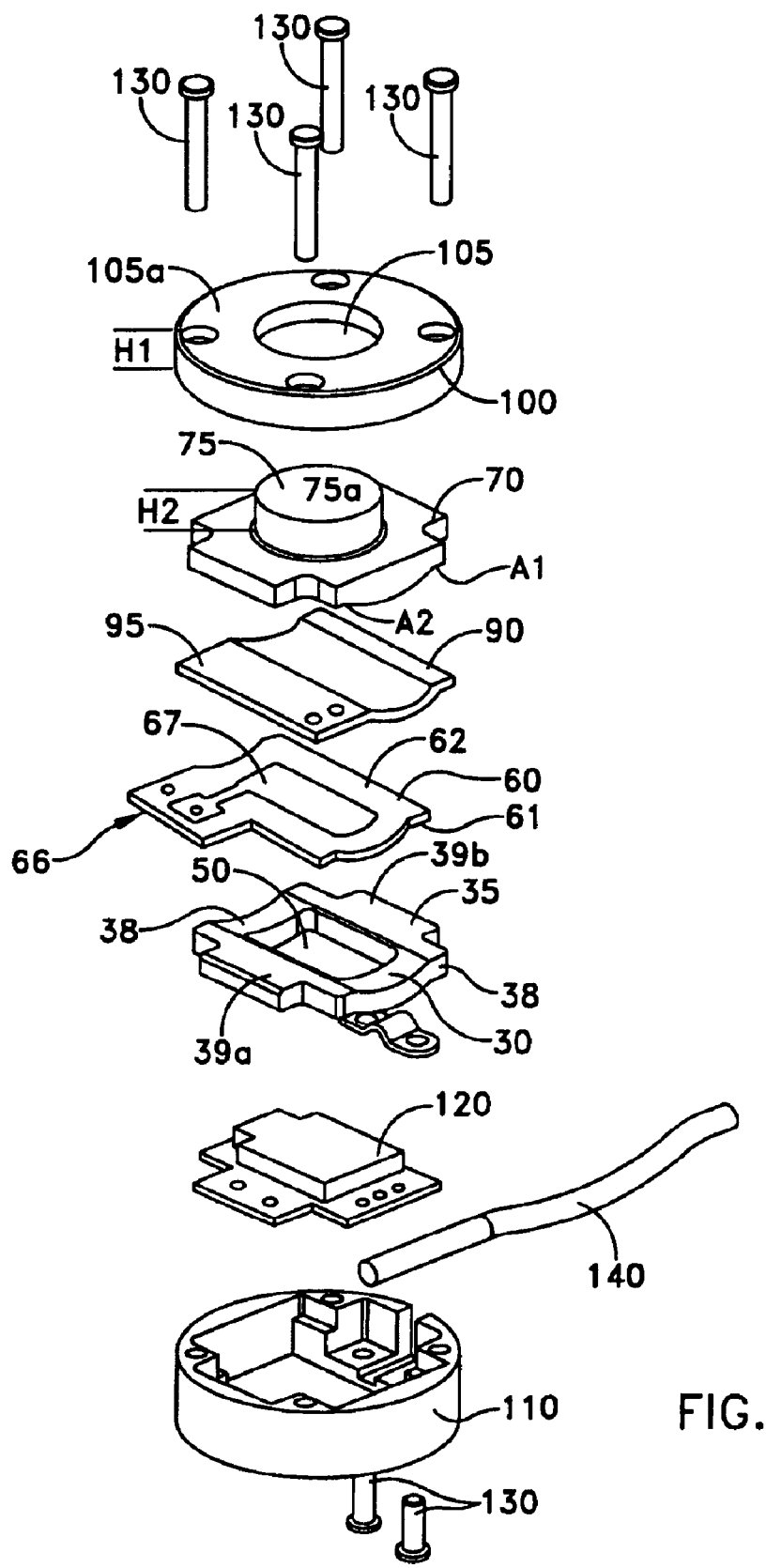
FIG. 9 is a perspective, exploded view of another embodiment of the acoustic sensor device illustrated in FIG. 4, having an alternative shielded sensing element structure.

FIG. 9 depicts another variation of the device shown in FIGS. 4–6, now incorporating the polymer film 90, for shielding the sensing element to reduce externally induced electrical noise. In this variation, the polymer film 90 is bonded to the PVDF film second surface and is now disposed between the PVDF film and the pliable layer 70. The bottom surface electrode 67 is an active electrode, while both the other film electrode 66 and the polymer film electrode 95 are grounded. This configuration is in contrast the to the alternate embodiment described above for FIGS. 8A–8C, where the polymer layer 90 is disposed between the substrate 30 and the PVDF film 60, and where the electrode 66 is active while electrode 67 is grounded.

The foregoing description of the embodiments of this invention has been presented for purposes of illustration and description. It is not intended to be exhaustive or to limit the embodiments of the invention to the form disclosed, and, obviously, many modifications and variations are possible. As an example, the piezoelectric film may comprise other materials that exhibit a piezoelectric effect such as, for example, a copolymer film. Such modifications and variations that may be apparent to a person skilled in the art are intended to be included within the scope of this invention as defined by the accompanying claims.

What is claimed is:

1. An acoustic sensor device comprising:
   a substrate having a first surface and a second surface opposite the first surface, and an aperture formed therethrough, the second surface having a curved portion;
   a layer of piezoelectric film having a first surface disposed on the curved portion of the substrate second surface; and
   a layer of pliable material disposed on a second surface of the piezoelectric film opposite the first surface for contacting with an object to be sensed.

2. The device of claim 1, further comprising a polymer layer disposed on a surface of the piezoelectric film.

3. The device of claim 1, wherein the piezoelectric film comprises PVDF.

4. The device of claim 1, wherein the substrate comprises a metal or plastic.

5. The device of claim 1, wherein the pliable layer comprises a material having an acoustic impedance substantially close to an acoustic impedance of the object to be sensed.

6. The device of claim 1, wherein the pliable layer comprises a rubber.

7. The device of claim 1, wherein the pliable layer comprises a polyurethane.

8. The device of claim 2, wherein the polymer layer is disposed between the piezoelectric film and the pliable layer.

9. An acoustic sensor device comprising:
  a substrate having a first surface and a second surface opposite the first surface, and an aperture formed therethrough, the second surface having a curved portion;
  a layer of piezoelectric film having a first surface disposed on the curved portion of the substrate second surface;
  a layer of pliable material disposed on a second surface of the piezoelectric film opposite the first surface for contacting with an object to be sensed; and,
  a housing having an opening through which a portion of said pliable material protrudes for contacting with an object to be sensed.

10. The device of claim 9, wherein the housing pressure clamps the first surface of the piezoelectric film to at least a non-curved portion of the substrate.

11. An acoustic sensor device comprising:
  a substrate having a first surface and a second surface opposite the first surface, and an aperture formed therethrough, the second surface having a curved portion;
  a layer of piezoelectric film having a first surface disposed on the curved portion of the substrate second surface;
  a layer of pliable material disposed on a second surface of the piezoelectric film opposite the first surface; and
  a housing for holding the substrate, piezoelectric film and pliable material, said housing having an opening through which a portion of said pliable material protrudes for contacting with an object to be sensed.

12. An acoustic sensor device comprising:
  a substrate having a first surface and a second surface opposite the first surface, and an aperture formed therethrough, the second surface having a curved portion;
  a layer of piezoelectric film having a first surface disposed on the curved portion of the substrate second surface;
  a layer of pliable material disposed on a second surface of the piezoelectric film opposite the first surface; and,
  a housing for holding the substrate, piezoelectric film and pliable material, said housing having an opening through which a portion of said pliable material protrudes for contacting with an object to be sensed;
  wherein the housing pressure clamps the first surface of the piezoelectric film to at least a non-curved portion of the substrate.

13. The device of claim 11, wherein the piezoelectric film comprises PVDF.

14. The device of claim 13, wherein the PVDF film has a thickness of 28–110 microns.

15. The device of claim 11, wherein the pliable layer comprises a rubber.

16. The device of claim 11, wherein the pliable layer comprises a polyurethane.

17. An acoustic sensor device comprising:
  a substrate having a first surface and a second surface opposite the first surface, and an aperture formed therethrough, the second surface having a curved portion;
  a layer of piezoelectric film having a first surface disposed on the curved portion of the substrate second surface;
  a layer of pliable material disposed on a second surface of the piezoelectric film opposite the first surface for contacting with an object to be sensed; and
  a polymer layer disposed on a surface of the piezoelectric film, for shielding of the piezoelectric film from electrical noise.

18. The device of claim 17, wherein the polymer layer is disposed between the piezoelectric film and the pliable layer.

19. The device of claim 17, wherein a grounded electrode is coupled to the first surface of the piezoelectric film.

20. A method of sensing an acoustic signal comprising:
  forming an acoustic sensor device comprising a substrate having a first surface and a second surface opposite the first surface and an aperture formed therethrough, and also comprising a layer of piezoelectric film having a first surface and a second surface opposite the first surface, the first surface being disposed on a curved portion of the substrate second surface and the second surface being disposed on a layer of pliable material;
  contacting said layer of pliable material with an object to be sensed;
  causing, through transmission of the sensed acoustic signal, an application of pressure on the piezoelectric film in a direction substantially normal to a surface of the film; and
  generating, through the piezoelectric effect of the film, an electrical signal indicative of said acoustic signal.

* * * * *